United States Patent [19]

Neesby

[11] Patent Number: 4,721,716

[45] Date of Patent: * Jan. 26, 1988

[54] METHOD FOR DESENSITIZING THE GASTROINTESTINAL TRACT FROM FOOD ALLERGIES

[76] Inventor: Torben E. Neesby, 2842 E. Griffith, Fresno, Calif. 93726

[*] Notice: The portion of the term of this patent subsequent to Jun. 26, 2003 has been disclaimed.

[21] Appl. No.: 738,883

[22] Filed: May 28, 1985

Related U.S. Application Data

[63] Continuation of Ser. No. 638,061, Aug. 6, 1984, abandoned.

[51] Int. Cl.$^4$ .................... A61K 31/19; A61K 31/525
[52] U.S. Cl. .................................... 514/251; 514/557; 514/558
[58] Field of Search ........................ 514/557, 558, 251

[56] References Cited

U.S. PATENT DOCUMENTS

| | | | |
|---|---|---|---|
| 3,088,866 | 5/1963 | Wernicoff et al. | 514/557 |
| 3,326,754 | 6/1967 | Prussin et al. | 514/557 |
| 3,564,098 | 2/1971 | Erwin et al. | 514/557 |
| 3,708,578 | 1/1973 | Das | 424/141 |
| 3,995,056 | 11/1976 | Allais et al. | 514/557 |
| 4,123,382 | 10/1978 | Morse et al. | 252/316 |

OTHER PUBLICATIONS

Chemical Abstracts, 67:63102R (1967).
Kirk–Othmer–Encyclopedia of Chem. Tech., 2nd ed., vol. 3, p. 881 (1964).

Primary Examiner—Leonard Schenkman
Attorney, Agent, or Firm—Lyon & Lyon

[57] ABSTRACT

There is disclosed a method for treatment of food allergies by desensitizing the gastrointestinal tract comprising the oral ingestion of a chemical composition wherein the composition comprises butyric acid or a salt thereof. It further may comprise $B_2$ vitamin riboflavin, ethyl cellulose as a time release preparation, and salts of capric, caproic and caprylic acids.

22 Claims, No Drawings

METHOD FOR DESENSITIZING THE GASTROINTESTINAL TRACT FROM FOOD ALLERGIES

This application is a continuation, of application Ser. No. 638,061, filed Aug. 6, 1984, abandoned.

BACKGROUND OF THE INVENTION

1. Field of the Invention

The field of the present invention relates generally to a method for treatment of food allergies in a human host having human food allergies and sensitivities by desensitizing the gastrointestinal tract and through this treatment, improved nutritional status and glandular and mental functions.

2. Description of the Prior Art

Food allergies are an important cause of illness in both children and adults. Allergies, including food allergies, remain the leading chronic diseases in patients under seventeen years old. Symptoms commonly known to accompany food allergies include headaches, stomach aches, depression, wheezing, fatigue, irritability, hyperactivity, skin rashes, drowsiness, and circles under the eyes. The incidence of allergy-related nutritional deficiencies is also significant due to the necessary avoidance of the offending foods.

Traditional treatment methods include injections and sublingual droplets of dilute extracts of the allergens which may cause anaphylactic shock. Food allergy sufferers may also be instructed to avoid a particular food, often disguised in the prepared foods so prevalent today. These treatments presuppose identification of the offending food.

Identification of food allergens is often elusive due to the time lag between ingestion and the onset of symptoms. Clinical identification methods, including trial elimination diets and food skin tests, are lengthy, costly and often inconclusive.

The present invention relieves sufferers from food allergies and its symptoms without the need to identify the particular allergen thereby avoiding the problematic identification procedures and expense as well as uncertainty associated therewith.

SUMMARY OF THE INVENTION

In the present invention, a method for the oral administration of a composition comprised of effective amounts of butyric acid or a non-toxic salt thereof is provided to alleviate and finally eliminate food allergies in a human host having human food allergies by desensitizing the gastrointestinal tract. Such salts may include lithium, sodium, potassium, calcium, magnesium, zinc, or sodium salts of capric, caproic, and/or caprylic acid. The B vitamins, particularly $B_2$ vitamin riboflavin, may be added to compensate for resultant B vitamin deficiency which may be associated with oral administration of butyric acid and/or salts thereof. A time-release preparation of ethyl cellulose or other accepted agents may also be added to the finely-powdered butyrates to prevent stomach irritation.

The advantages of the present invention include:

(1) effectiveness without regard to problematic and expensive identification of the offending food;

(2) no risk of anaphylactic shock present as with conventional diagnosis and treatment of food allergies since its constituents are considered foods and no restrictions are limiting their use in nutrition;

(3) concurrent benefits such as greater emotional stability and feeling of well-being; and (4) ability to complement with the recognized anti-anxiety remedies such as tranquilizers or other medications such as antifungal agents.

In its preferred embodiment, the method comprises the oral administration of a composition of butyric acid or a watersoluble non-toxic salt thereof in their respective effective amounts. Butyric acid is operable per se in this invention. The salts of butyric acid are, however, preferred to the acid per se or its esters because they have less offensive odor and flavor. Such salts include lithium, sodium, potassium, calcium, magnesium, or zinc. The magnesium and calcium salts are particularly preferred to those of sodium or potassium salts because the cations of these salts are only partially absorbed by the gastrointestinal tract and this eases the load on the kidneys, a load which is caused by the alkalosis created when butyric acid metabolizes into $CO_2$ and is expelled through the lungs leaving the alkaline cations to be excreted through the kidneys. ("Butyrate" hereinafter refers to butyric acid or a salt thereof.)

In the practice of the present invention, it is preferred that the mixture further comprise $B_2$ vitamin riboflavin in the amount of at least about 25 mg. up to about 100 mg. per 500 mg. butyrate to compensate for riboflavin deficiency, which may be caused by increased metabolism of butyrate.

It is also preferred that the mixture further comprise an enteric coating material on the butyrate granules for time release delaying action to alleviate possible stomach irritation caused by butyrate intake. Suitable time release material for the practice of the present invention includes ethyl cellulose. However, it will be obvious to one skilled in the art that other types of time releasing preparations may also be utilized in connection with the practice of the present invention. By way of example only, U.S. Pat. No. 3,849,558, the disclosure of which is incorporated herein by reference, makes known a composition and method wherein pharmaceutical compositions with controlled rates of gastrointestinal absorption are prepared by dissolution or suspension of the therapeutically active agent in an absorption depressive agent.

Coated butyrate with or without riboflavin may also be used in combination with individual or combinations of effective amounts of sodium salts of capric acid, caproic acid, and caprylic acid as long as the mixtures contain at least about 40% butyrate.

In accordance with the method of this invention, butyrate is administered orally in either tablet or capsule form. The normal dosage required is in an amount of one to two grams of butyrate for each dose to be administered. However, of course, this dosage may vary depending upon the age and weight of the subject. A dose should preferably be taken at each meal for a total daily intake of about 3 to about 10 grams butyrate. Desensitization is seen in about 1 to 2 weeks whereas improvements in glandular functions have been observed after longer administration time.

The following examples will aid in explaining the preparation of the various salts of the present invention but are intended to be illustrative only, and not limiting:

EXAMPLE 1

40 g. of sodium hydroxide were dissolved in 100 ml. of water and cooled to 30° C. 88 g. of butyric acid were stirred slowly into the sodium hydroxide solution. The pH of the solution was adjusted to 7.2 by addition of either sodium hydroxide or butyric acid. The sodium butyrate was then cooled, cut into small pieces, and dried. The dried sodium butyrate was ground to a granulated condition and the mixture was filled into a size 00 gelatin capsule accommodating 500 to 600 mg. sodium butyrate.

EXAMPLE 2

40 g. of magnesium oxide and 82 g. of calcium hydroxide were added to 400 ml. water. While stirring the mixture, 370 g. of butyric acid were added. The salts were maintained at a high temperature and continually stirred until they had attained a smooth condition. The pH was adjusted to 7.4. The mixture was cooled and spread on a glass tray which was placed in a drying oven until the mixture became dry and then was ground and granulated.

EXAMPLE 3

56 g. of potassium hydroxide were dissolved in 70 ml. water and the solution was cooled to about 20° C. 88 g. of butyric acid were added slowly with stirring. Potassium butyrate was vacuum dried and then ground finely and granulated.

EXAMPLE 4

One gram mole of sodium hydroxide was dissolved in 100 ml water. The equivalent weight of caproic acid was added to the solution. The mixture was then dried and added to butyrate as prepared in Examples 1, 2, and 3.

EXAMPLE 5

Example 4 was repeated except that caprylic acid was substituted for caproic acid.

EXAMPLE 6

Example 4 was repeated except that capric acid was substituted for caproic acid. A mixture was then made comprising, by way of example only, 50% butyrate, 5% caproate, 20% caprylate, and 20% caprate.

EXAMPLE 7

An alcoholic solution of ethyl cellulose was then added to the dried finely powdered mixture of butyrate as prepared in Examples 1 through 6 in sufficient amounts to give a final granulation containing from about 15% to about 30% of ethyl cellulose.

EXAMPLE 8

50 g. of $B_2$ vitamin riboflavin was added to 1,000 g. of dried granulated butyrate as prepared in Examples 1 through 6.

The following are case histories of the treatment with calcium magnesium buytrate of persons with food intolerances. The proportion of calcium to magnesium is 2:1. It is to be understood that these histories are given by way of illustration and not of limitation.

CASE HISTORY NO. I

Male, age 71. Improvement was seen within a week and in three months, the subject was markedly relieved of his food sensitivity. The 2:1 mixture of calcium-magnesium butyrate was administered in combination with the anti-fungal drug, Nystatin.

CASE HISTORY NO. II

Female, age 68, with a long history of food sensitivities. Markedly relieved from symptoms after treatment for three months.

CASE HISTORY NO. III

Female with a long history of disabling migraine headaches. Practically free of headaches after two months of treatment.

CASE HISTORY NO. IV

Male with multiple food sensitivities, especially to wheat products. Treatment allowed subject to achieve desired weight gain.

CASE HISTORY NO. V

Male, age 21, with multiple food sensitivities. Receiving allergy shots for 37 food components. These combined with the calcium-magnesium butyrate treatment allowed the subject increased food choices.

CASE HISTORY NO. VI

Female with multiple food allergies. When treated in combination with allergy shots, her food choices were increased.

CASE HISTORY NO. VII

Male with wheat and cheese sensitivity. When treated in combination with an anti-allergenic amino acid mix, he became symptom free.

CASE HISTORY NO. VIII

Female, age 28, with wheat sensitivity causing an arthritic-like condition. Has been getting homeopatic treatment and in combination with the calcium-magnesium butyrate, the subject was markedly relieved of her food sensitivity.

Having fully described the present invention, it will be apparent from the above description that various modifications may be made within the scope of the invention. Therefore, the invention is not intended to be limited except as may be required by the lawful scope of the following claims.

What is claimed is:

1. A method for treating food allergies in a human host having human food allergies comprising the oral administration of a composition comprised of an effective amount of butyric acid.

2. A method as recited in claim 1 wherein the composition further comprises B vitamins.

3. A method as recited in claim 1 wherein the composition is comprised of about 25 mg. up to about 100 mg. riboflavin per 500 mg. butyric acid.

4. A method as recited in claim 1 wherein the composition further comprises a time release preparation.

5. A method as recited in claim 4 wherein said preparation is ethyl cellulose.

6. A method as recited in claim 1 wherein the composition is ingested before each meal.

7. A method as described in claim 1 wherein each dose is about 1 to about 2 grams of the composition comprised of butyric acid.

8. A method as described in claim 1 wherein the total daily intake of the composition of butyric acid is about 3 grams to about 10 grams.

9. A method as recited in claim 1 wherein the composition is administered at least three times a day for at least about one-week.

10. A method for treating food allergies in a human host having human food allergies comprising the oral administration of a composition comprised of an effective amount of butyric acid or at least one salt thereof.

11. A method as recited in claim 10 wherein the salt is selected from the group consisting lithium butyrate, sodium butyrate, potassium butyrate, calcium butyrate, magnesium butyrate, or zinc butyrate.

12. A method as recited in claim 10 wherein at least one salt is a sodium salt.

13. A method as recited in claim 12 wherein the sodium salt is selected from the group consisting of a sodium salt of capric acid, a sodium salt of caproic acid or a sodium salt of caprylic acid.

14. A method as recited in claim 10 wherein the composition further comprises B vitamins.

15. A method as recited in claim 10 wherein the composition is comprised of about 25 mg. up to about 100 mg. riboflavin per 500 mg. butyric acid or at least one salt thereof.

16. A method as recited in claim 10 wherein the composition further comprises a time release preparation.

17. A method as recited in claim 16 wherein said preparation is ethyl cellulose.

18. A method as recited in claim 10 wherein the composition is further comprised of butyric acid.

19. A method as recited in claim 10 wherein the composition is ingested before each meal.

20. A method as described in claim 10 wherein each dose is about 1 to about 2 grams of the composition comprised of butyric acid or at least one salt thereof.

21. A method as described in claim 10 wherein the total daily intake of the composition of butyric acid or at least one salt thereof is about 3 grams to about 10 grams.

22. A method as recited in claim 10 wherein the composition is administered at least three times a day for at least about one week.

* * * * *